(12) United States Patent
Saka (10) Patent No.: US 8,761,656 B2
(45) Date of Patent: Jun. 24, 2014

(54) EDGE DETECTING DEVICE AND IMAGE FORMING APPARATUS INCLUDING THE SAME

(75) Inventor: Keisuke Saka, Ibaraki (JP)

(73) Assignee: Ricoh Company, Limited, Tokyo (JP)

( * ) Notice: Subject to any disclaimer, the term of this patent is extended or adjusted under 35 U.S.C. 154(b) by 90 days.

(21) Appl. No.: 13/413,769

(22) Filed: Mar. 7, 2012

(65) Prior Publication Data

US 2012/0237226 A1   Sep. 20, 2012

(30) Foreign Application Priority Data

Mar. 18, 2011   (JP) .................................. 2011-061686

(51) Int. Cl.
*G03G 15/00* (2006.01)
*G01N 21/86* (2006.01)
*G01N 21/84* (2006.01)

(52) U.S. Cl.
CPC ................ *G03G 15/00* (2013.01); *G01N 21/84* (2013.01); *G03G 15/607* (2013.01); *G01N 21/86* (2013.01)
USPC ........................ 399/389; 250/559.36; 356/429

(58) Field of Classification Search
CPC .................. B65H 2553/414; B65H 2553/416; B65H 7/14; B65H 2553/412; B65H 2553/41
USPC ........................ 250/559.36; 399/389; 356/429
See application file for complete search history.

(56) References Cited

U.S. PATENT DOCUMENTS

| | | | | |
|---|---|---|---|---|
| 7,115,889 B2 * | 10/2006 | Koker et al. | ............. | 250/559.36 |
| 7,276,719 B2 * | 10/2007 | Schwarz | ................... | 250/559.36 |
| 2003/0209680 A1 * | 11/2003 | Burkatovsky | ............. | 250/559.36 |
| 2006/0214118 A1 * | 9/2006 | Hiura | ......................... | 250/492.2 |
| 2006/0232759 A1 * | 10/2006 | Fukube et al. | ................ | 355/408 |
| 2010/0309488 A1 * | 12/2010 | Koyama et al. | ............... | 356/908 |

FOREIGN PATENT DOCUMENTS

| | | |
|---|---|---|
| JP | 9-106236 | 4/1997 |
| JP | 2007-119135 | 5/2007 |
| JP | 2008-87934 | 4/2008 |
| JP | 4794979 | 8/2011 |

\* cited by examiner

*Primary Examiner* — Daniel J Colilla
*Assistant Examiner* — John M Royston
(74) *Attorney, Agent, or Firm* — Oblon, Spivak, McClelland, Maier & Neustadt, L.L.P.

(57) ABSTRACT

An edge detecting device for detecting an edge of a moving recording medium includes a reflecting unit that includes a reflecting surface having reflectance higher than that of the recording medium, light sources that irradiate the recording medium and the reflecting surface of the reflecting unit with light, a light receiving unit that includes pixels of a photoelectric conversion element provided in a width direction of the recording medium and receives reflected light that has been emitted from the light sources and has been reflected by the recording medium and the reflecting surface of the reflecting unit on the pixels of the photoelectric conversion element, and a control unit that determines a region of the pixels of the photoelectric conversion element that make output higher than a previously set determination threshold value to be the edge of the recording medium on the light receiving unit.

15 Claims, 8 Drawing Sheets

EDGE DETECTING DEVICE AND IMAGE FORMING APPARATUS INCLUDING THE SAME

CROSS-REFERENCE TO RELATED APPLICATIONS

The present application claims priority to and incorporates by reference the entire contents of Japanese Patent Application No. 2011-061686 filed in Japan on Mar. 18, 2011.

BACKGROUND OF THE INVENTION

1. Field of the Invention

The present invention relates to an edge detecting device that detects an edge of a recording medium and an image forming apparatus including the edge detecting device.

2. Description of the Related Art

In an image forming apparatus of electrophotography, there has been a known technology of correcting main-scanning registration for each piece of recording media and a technology of calculating a skew amount from a detected edge of a recording medium by arranging an optical detecting unit such as a contact image sensor (hereinafter, referred to as a CIS) for detecting an edge of the recording medium (hereinafter, referred to as an "edge") on a conveying path of the recording medium and by calculating a deviation amount of main-scanning registration from a detected edge position of the recording medium so as to adjust a transfer position relative to the recording medium or to adjust a position of the recording medium based on the transfer position.

An edge detection of a recording medium by a detecting unit of an optical system is performed by applying light emitted from a light source such as a light emitting diode (LED) included in the detecting unit onto the recording medium and by receiving reflected light reflected by the recording medium with a light receiving unit included in the detecting unit. For example, Japanese Patent Application Laid-open No. 2007-119135 discloses a configuration in which a CIS or the like having an LED as a light source is used as a detecting unit for detecting an edge of a recording medium and a light emission amount of the LED is adjusted so as to detect the edge of the recording medium.

In a conventional method for detecting an edge of a recording medium, detection light is applied onto the recording medium that is a detection target from a detecting unit of an optical system and reflected light reflected by the recording medium is received by a light receiving unit. Then, a processing unit processes in such a manner that the recording medium is determined to be present on a pixel that has received a greater amount of light than a threshold value and a recording medium is determined not to be present on a pixel that has not received a greater amount of light than the threshold value. Furthermore, a boundary between these pixels is detected to be the edge of the recording medium. Therefore, reflection by the recording medium may be insufficient depending on the wavelength of light emitted from a light source of the detecting unit to be used and conditions originating from the recording medium, such as the material properties or the color of the recording medium. In such a case, the detecting unit may receive the reflected light with the amount that does not exceed the threshold value even on a portion on which the recording medium is present, thereby making the determination on whether or not the recording medium ambiguous. Therefore, it is difficult to detect an edge of the recording medium with high accuracy.

Japanese Patent Application Laid-open No. 2007-119135 discloses a technology in which the CIS or the like is arranged for detecting an edge of a recording medium and a light emission amount of the LED is adjusted so as to detect the edge of the recording medium properly. However, there are problems which cannot be solved easily. For example, choice on the light emission wavelength of a light source of a detecting unit (CIS) to be used and the reflectance property of the recording medium may make it difficult to detect an edge of a recording medium. Furthermore, detection of an edge of a recording medium having low reflectance requires the light emission time of the light source to be longer and the light emission intensity of the light source to be higher, thereby to shorten the lifetime of the light source and to increase detection time needed for detecting the edge of the recording medium.

Thus, there is a need to provide an edge detecting device that can detect edges of various types of recording media accurately in a short period of time independent of the emission wavelength of the light emitted from a light source or reflectance properties of the recording media.

There is also a need to provide an image forming apparatus that has high paper handling capacity and can realize a preferable image by achieving high accuracy in detecting edges of recording media in a short period of time even when various types of recording media are used.

SUMMARY OF THE INVENTION

It is an object of the present invention to at least partially solve the problems in the conventional technology.

An edge detecting device for detecting an edge of a moving recording medium includes: a reflecting unit that includes a reflecting surface having reflectance higher than reflectance of the recording medium; a light source that irradiates the recording medium and the reflecting surface of the reflecting unit with light; a light receiving unit that includes a plurality of pixels of a photoelectric conversion element arranged in a width direction of the recording medium and receives reflected light that has been emitted from the light source and has been reflected by the recording medium and the reflecting surface of the reflecting unit on the pixels of the photoelectric conversion element; and a control unit that determines a region of the pixels of the photoelectric conversion element that makes output higher than a preset determination threshold value in the light receiving unit as the edge of the recording medium.

An image forming apparatus includes: a transfer unit that transfers a toner image formed on an image carrier; a conveying path on which a recording medium housed in a paper feeding unit is conveyed toward the transfer unit, and an edge detecting unit that is provided upstream of the transfer unit in a recording medium moving direction and detects an edge of a recording medium that is moving. The edge detecting unit is the edge detecting unit as mentioned above.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An edge detecting device according to the present embodiment has the following characteristics in a process of detecting an edge of a recording medium. That is, a high reflectance member (for example, a reflecting mirror) is mounted on a lower portion of a CIS at an angle at which the member can receive more reflected light. Light emitted from the CIS is caused to be reflected by the high reflectance member and the recording medium, and the reflected light is received by the CIS. With this configuration, the intensity of the light reflected by the high reflectance member is higher than that of the light reflected by the recording medium. Therefore, it can be determined that no recording medium is present on a pixel of a photoelectric conversion element having received more reflected light than a threshold value and that the recording medium is present on another pixel of the photoelectric conversion element having received less reflected light than the threshold value. These characterize the edge detecting device according to the present embodiment in which a boundary between the pixels of the photoelectric conversion element is detected as an edge of the recording medium.

The present embodiment is described in detail with reference to drawings.

Figure 1:
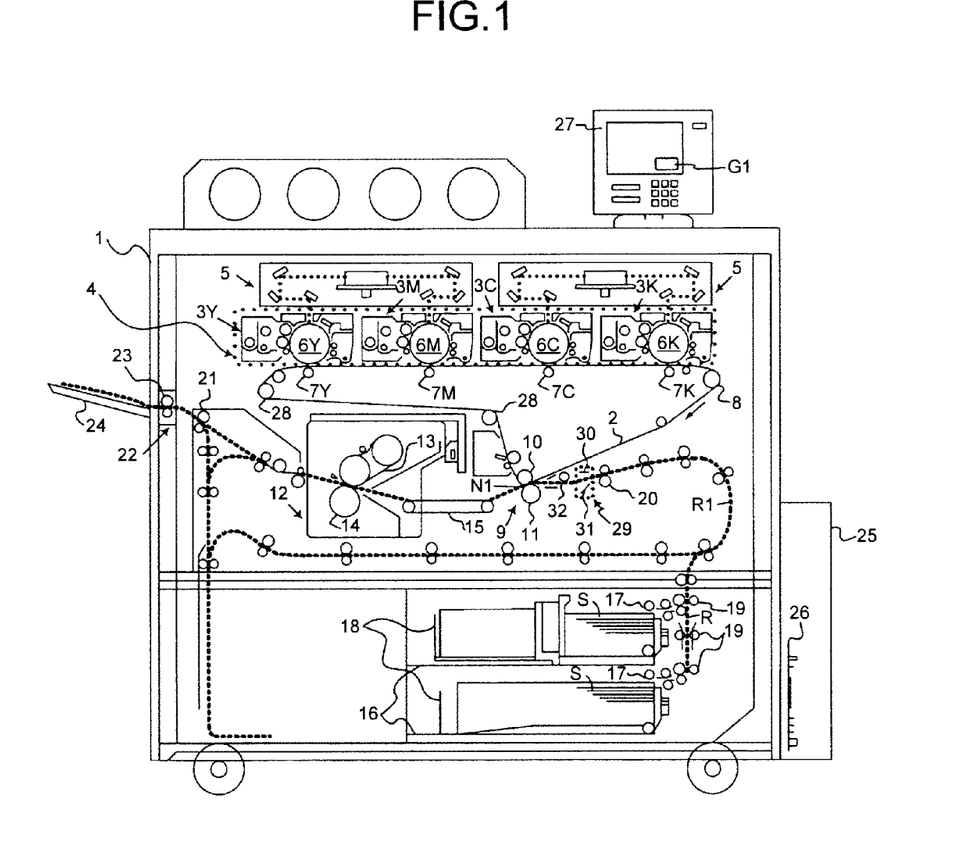
FIG. 1 is a view illustrating a schematic configuration of an image forming apparatus according to an embodiment.

A color printer as illustrated in FIG. 1 is a form of an image forming apparatus to which the present embodiment is applied. The image forming apparatus is not limited to the color printer and a monochrome printer, a copying machine, a facsimile, or a complex machine including these functions may also be used.

The color printer can form a full color image by using toners of four colors including yellow (Y), magenta (M), cyan (C), and black (K). An intermediate transfer belt 2 serving as an endless belt-shaped image carrier is provided in a vicinity of a center of an apparatus main body 1. The intermediate transfer belt 2 is wound around a plurality of supporting rollers 28, a driving roller 8, and a secondary transfer opposing roller 10, and is configured to be capable of performing rotational conveyance in a clockwise direction in FIG. 1 when the driving roller 8 is rotationally driven by a driving motor (not illustrated). Above the intermediate transfer belt 2, a tandem-type image forming portion 4 is configured by disposing a plurality of image forming units 3Y, 3M, 3C, 3K corresponding to the colors of yellow (Y), magenta (M), cyan (C), and black (K) side by side along the moving direction of the intermediate transfer belt 2. Two exposing devices 5, 5 are provided above the tandem-type image forming portion 4. The image forming units 3Y, 3M, 3C, and 3K include photosensitive elements 6Y, 6M, 6C, and 6K as latent image carriers that carry toner images of the corresponding colors.

Primary transfer rollers 7Y, 7M, 7C, and 7K serving as constituent elements of a primary transfer unit are provided at primary transfer positions so as to be opposed to the respective photosensitive elements by interposing the intermediate transfer belt 2 therebetween. The primary transfer positions are the positions where the toner images are transferred from the photosensitive elements 6Y, 6M, 6C, and 6K onto the intermediate transfer belt 2.

An operator panel 27 on which various settings such as print setting and operations are performed by a customer is provided at an upper portion of the apparatus main body 1.

An edge detecting device 29 and a secondary transfer unit are provided below the intermediate transfer belt 2. A secondary transfer unit 9 in FIG. 1 is a well-known unit that transfers the toner images on the intermediate transfer belt 2 onto a recording medium S in such a way that a power supply (not illustrated) applies a transfer electric field for secondary transfer to a secondary transfer nip N1 serving as a transfer unit that is formed by pressing a secondary transfer roller 11 against the secondary transfer opposing roller 10 from an outer side of the intermediate transfer belt 2.

In FIG. 1, a fixing portion 12 is provided next to the secondary transfer unit 9 with a conveying belt 15 provided therebetween. In the fixing portion 12, a fixing nip is formed by pressing a pressing roller 14 against a fixing belt 13 that is an endless belt. The fixing method used in the fixing portion 12 is a well-known method for fixing the transferred image that has been transferred onto the recording medium S having been conveyed by the conveying belt 15 by applying heat and pressure.

The edge detecting device 29 is provided on a conveying path R1 at an upstream side of the secondary transfer nip N1 in the recording medium moving direction. The edge detecting device 29 is formed by a CIS 30 mainly serving as an optical detecting unit and a reflecting mirror 31 serving as the reflecting unit. The edge detecting device 29 irradiates a recording medium S passing through the conveying path R1 and the reflecting mirror 31 with light irradiated from the CIS 30 and receives the reflected light reflected by the recording medium S and the reflecting mirror 31.

In the image forming apparatus, image data is transmitted from a controller board 26 provided in a controller box 25 that is provided on a side surface of the apparatus main body 1. When the image forming apparatus receives a signal for instructing to start image formation, the driving roller 8 is rotationally driven by a driving motor (not illustrated) and the supporting rollers 28 are rotationally driven so that the intermediate transfer belt 2 is rotationally conveyed. At the same time, a single color image is formed on each of the photosensitive elements 6Y to 6K by each of the image forming units 3Y to 3K. Furthermore, when the intermediate transfer belt 2 is conveyed, the single color toner images formed on the photosensitive elements are sequentially transferred onto the intermediate transfer belt 2 at the primary transfer positions so as to form a composite color image on the intermediate transfer belt 2.

A paper feed table 16 that includes a plurality of paper feed cassettes 18 serving as paper feeding units is provided at a lower portion of the apparatus main body 1. On the paper feed table 16, if the paper feed cassette 18 is selected and the apparatus is operated to form an image, paper feed rollers 17 are rotated and a recording medium S is fed from one of the paper feed cassettes 18 to a conveying path R connected to the conveying path R1. The recording medium S fed by a registration roller 20 is conveyed to the conveying path R1 by carriage rollers 19 provided on the conveying path R. Then, the recording medium stops by abutting on the registration roller 20 provided at an upstream side of the edge detecting device 29 in the recording medium moving direction. The registration roller 20 rotates by being synchronized with timing of the composite color image on the intermediate transfer belt 2. A shift roller 32 is provided between the edge detecting device 29 and the secondary transfer nip N1. The shift roller 32 is shift-driven in the main-scanning direction based on a registration deviation amount in the main-scanning direction so as to correct a position of the recording medium S. Here, the registration deviation amount in the main-scanning direction is calculated from an edge Sa of the recording medium S detected by the edge detecting device 29. At the secondary transfer nip N1, the toner image is transferred onto the recording medium S after the position thereof is corrected.

After the image has been transferred onto the recording medium S, the recording medium S is conveyed to the fixing portion 12 by a conveying action of the secondary transfer nip N1 and the conveying belt 15; and heat and pressure are applied thereto so that the transferred image (toner image) is fixed. Thereafter, the recording medium S is conveyed to a decurler unit 22 that corrects warpage of the recording medium S by using the discharge roller 21 in a well-known manner. Then, the recording medium S is discharged to the outside of the apparatus main body 1 while being corrected by a decurler roller 23 of the decurler unit 22 and is stacked onto a discharge tray 24.

Figure 2:
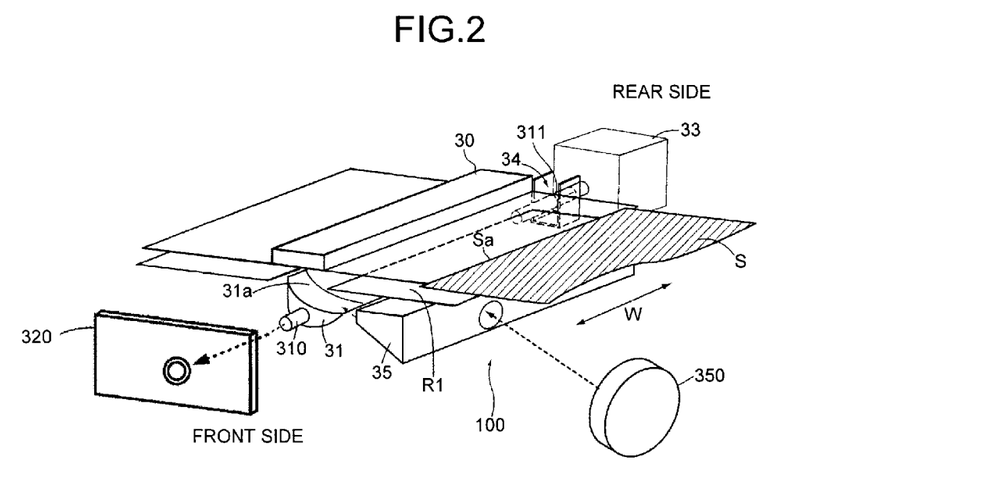
FIG. 2 is a perspective view illustrating a schematic configuration of an edge detecting device.

FIG. 2 illustrates a form of a mechanical configuration of the edge detecting device 29. The edge detecting device 29 includes the CIS 30, the reflecting mirror 31, a stepping motor 33 serving as a driving unit of the reflecting mirror 31, a light shielding sensor 34 that is a position detecting unit of the reflecting mirror 31 and also functions as a detecting unit that detects the presence of the reflecting unit, and a blowing port 35 of the air sent from a blower fan 350. The blowing port 35 is provided to be capable of being opposed to a reflecting surface 31a of the reflecting mirror 31 so that the air sent from the blower fan 350 blows the reflecting surface 31a of the reflecting mirror 31.

Figure 3:
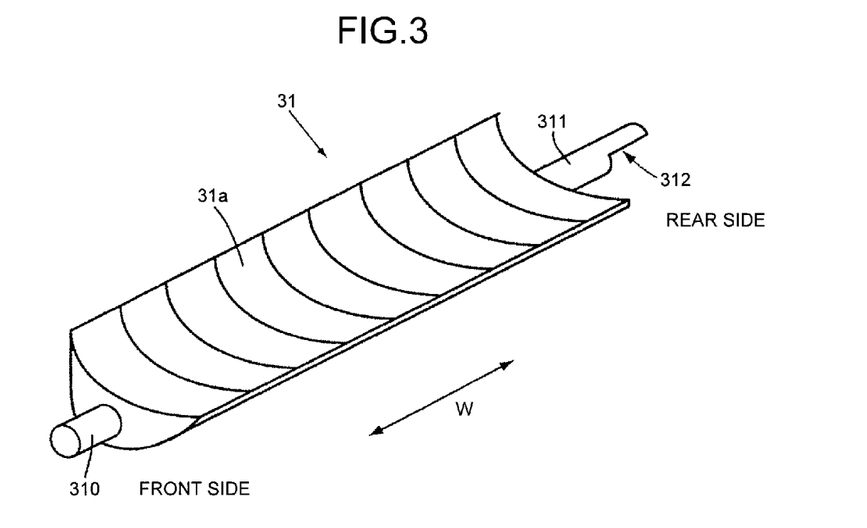
FIG. 3 is a perspective view illustrating a configuration of a reflecting unit included in the edge detecting device.
Figure 4:
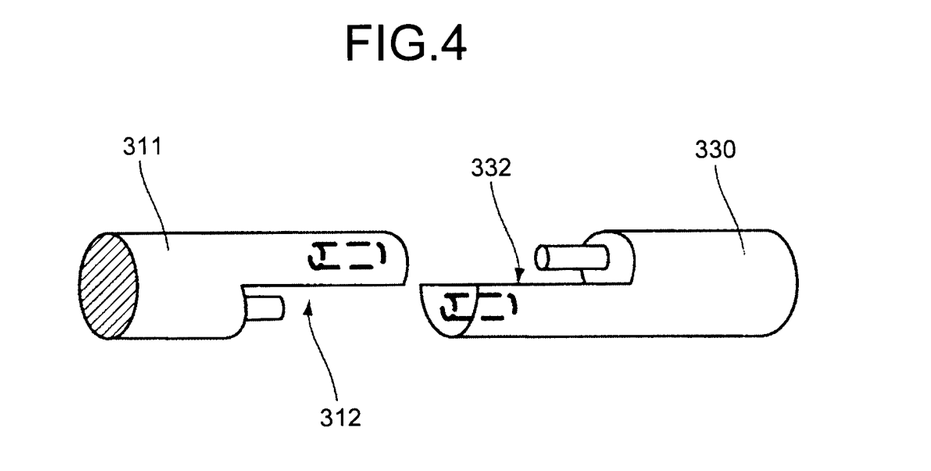
FIG. 4 is an enlarged perspective view illustrating a form of a coupling portion between the reflecting unit and a driving source.

The CIS 30 and the reflecting mirror 31 are provided so as to face the conveying path R1 and so as to be opposed to each other with respect to the conveying path R1. As illustrated in FIG. 3, the reflecting mirror 31 extends in a width direction W of the recording medium S. Shafts 310 and 311 protrude coaxially in the width direction from both ends of the reflecting mirror 31 on a front side and a rear side, respectively, of the apparatus main body 1. The shaft 310 is provided on the front side and is rotatably supported by a sheet-metal frame 320 serving as a detecting device main body provided on the front side through a bearing (not illustrated). The sheet-metal frame 320 is detachably supported on the apparatus main body 1 and is firmly fixed to the apparatus main body 1 with a screw or the like (not illustrated). As illustrated in FIG. 4, the shaft 311 is coupled to an output shaft 330 of the stepping motor 33 provided on the rear side of the apparatus main body 1. That is to say, the shaft 311 of the reflecting mirror 31 and the output shaft 330 of the stepping motor 33 have symmetric shapes to each other; half of a tip along a circumference is cut out from each of the shaft 311 and the output shaft 330 and cut surfaces thereof are referred to as faying surfaces 312, 332, respectively. A recess-protrusion engagement portion formed by a pin and a hole that extend in a shaft line direction is formed on each of the faying surfaces 312 and 332. Furthermore, if the pins are inserted into the corresponding holes, the faying surfaces 312 and 332 can be integrally rotated in the rotational direction and mechanically coupled to each other detachably in the shaft line direction.

Therefore, if the sheet-metal frame 320 is detached from the apparatus main body 1, the reflecting mirror 31 can be detached together with the sheet-metal frame 320 from the front side (an operator's side). Furthermore, the reflecting mirror 31 can be attached from the front side (the operator's side) to the rear side.

Figure 5:
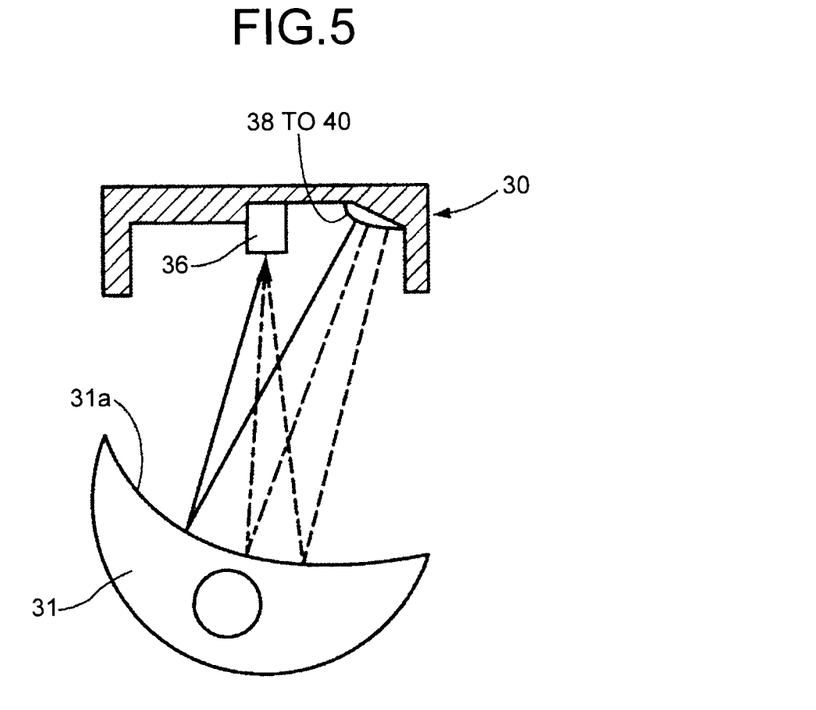
FIG. 5 is an explanatory diagram for illustrating a positional relationship between reflected light reflected by the reflecting unit and a light receiving unit.

As illustrated in FIG. 3, the reflecting mirror 31 according to the present embodiment has the reflecting surface 31a that is not a flat surface but a paraboloid curved inward. As illustrated in FIG. 5, the reflecting surface 31a having the paraboloidal shape reflects light emitted from light sources 38 to 40 included in the CIS 30, to be described later. Furthermore, the reflecting surface 31a is formed in a curved manner such that the reflected light is concentrated onto a light receiving unit 36 included in the CIS 30 linearly in the width direction thereof. In the present embodiment, the reflecting surface 31a is formed so as to have reflectance higher than that of the recording medium S that is expected to be used in the color printer.

The shaft 310 of the reflecting mirror 31 and the output shaft 310 of the stepping motor 33 are coupled to each other. Therefore, if the stepping motor 33 is driven, the reflecting mirror 31 becomes rotatable. As a result, a reflection angle of the reflecting surface 31a becomes adjustable. Thus, the stepping motor 33 functions as an angle adjusting unit. The light shielding sensor 34 detects whether or not the shaft 311 of the reflecting mirror 31 is present and a rotation amount of the shaft 311. Therefore, the light shielding sensor 34 functions as a presence detecting unit of an attachment state of the reflecting mirror 31 to the edge detecting device 29 and a rotation angle detecting unit of the reflecting mirror 31.

In the present embodiment, the reflection angle of the reflecting surface 31a can be adjusted by controlling the rotation angle of the stepping motor 33, and cleaning of the reflecting surface 31a by removing paper powder and the like attached thereto can be performed by driving the blower fan 350 in a state in which the reflecting surface 31a and the blowing port 35 are caused to be opposed to each other, so that the air is blown to the reflecting surface 31a through the blowing port 35. Furthermore, by configuring the reflecting mirror 31 to be detachable at a predetermined angle position, an operator or a service person can perform cleaning manually by rotationally moving the reflecting mirror 31 by using the stepping motor 33. That is to say, the stepping motor 33 and the blower fan 350 configure a cleaning unit 100.

When the blower fan 350 is driven to send the air to the reflecting surface 31a, the stepping motor 33 is driven to move the reflecting mirror 31 to a predetermined angle at which the air ejected through the blowing port 35 blows the reflecting mirror 31. The cleaning operation formed by the rotational movement of the reflecting mirror 31 caused by the stepping motor 33 and driving of the blower fan is performed in a cleaning mode M5. The cleaning mode M5 may be performed by providing an operation switch G1 for selecting the cleaning mode M5 on the operator panel 27 as illustrated in FIG. 1 and by presetting the cleaning mode M5 in a control device 300 such that the cleaning mode M5 is performed if the operation switch G1 is operated. Alternatively, the cleaning mode M5 may be automatically performed if the cleaning mode M5 has not been performed.

In the present embodiment, the reflecting mirror 31 is configured to be detachable. Therefore, the edge of the recording medium S can be detected not only by using the reflecting mirror 31 but also by a conventional detecting method by detaching the reflecting mirror 31.

Figure 6:
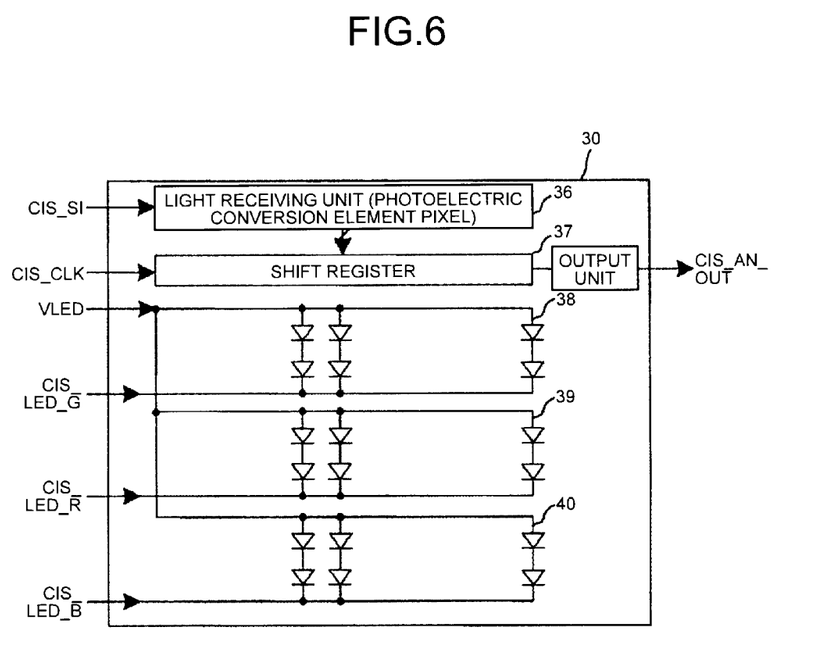
FIG. 6 is a schematic diagram illustrating a configuration of a detecting unit of the edge detecting device according to the present embodiment.
Figure 8:
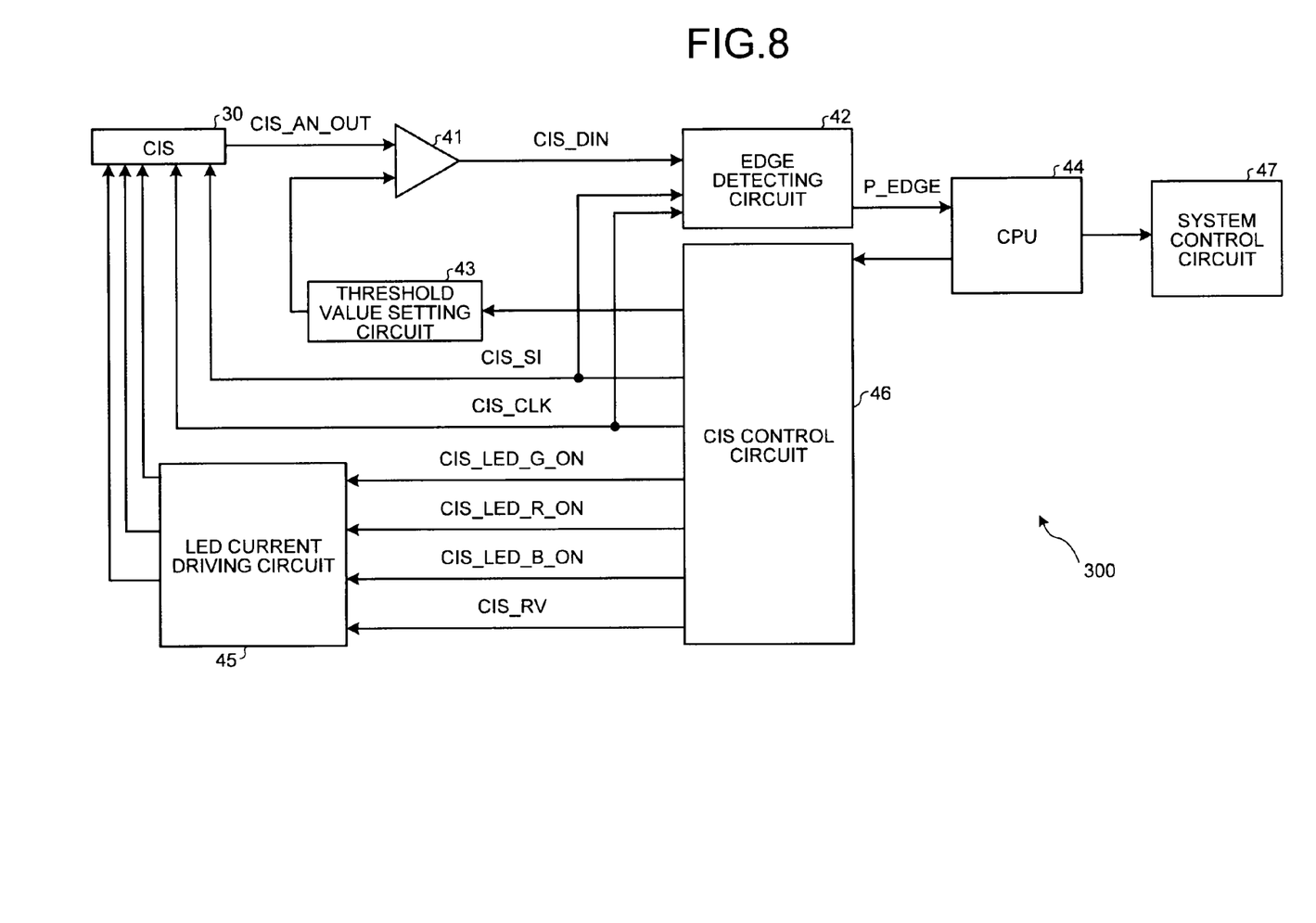
FIG. 8 is a block circuit diagram illustrating a control unit that includes an edge detecting circuit for a recording medium according to the present embodiment.

FIG. 6 is a schematic diagram illustrating a configuration of the CIS 30 according to the present embodiment. In FIG. 6, the CIS 30 mainly includes the light receiving unit 36, a shift register 37, the light source (LED-Green) 38, the light source (LED-Red) 39, and the light source (LED-Blue) 40. The light receiving unit 36 is formed by a plurality of pixels of the photoelectric conversion element arranged in the width direction W of the recording medium S. Light amounts (output levels) of the light sources 38 to 40 formed by LEDs of three colors including red, green, and blue are adjusted by causing a LED current driving circuit 45 provided on an outside of the CIS 30 as illustrated in FIG. 8 to drive signals of CIS_LED_G, CIS_LED_B, and CIS_LED_R. The LED current driving circuit 45 functions as a light amount adjusting unit.

Figure 7:
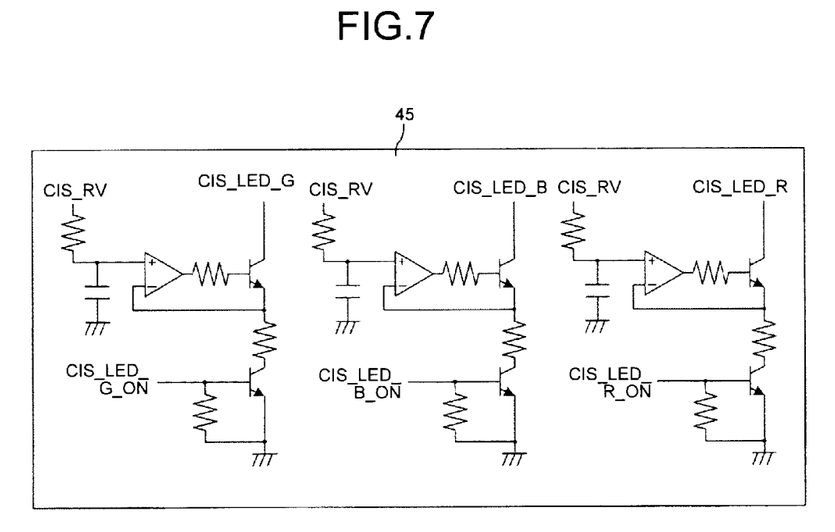
FIG. 7 is a driving circuit diagram illustrating a light source of the edge detecting device according to the present embodiment.

FIG. 7 illustrates an example of a driving circuit (LED current driving circuit 45) of the CIS_LED (R, G, B) signals for constant current driving. In the constant current driving, for example, the CIS_LED (R, G, B) signals are driven with a direct current (DC) by the LED current driving circuit 45 as illustrated in FIG. 7. In the circuit, a maximum current value flowing in the LEDs of the light sources 38 to 40 is predetermined by resistors. Each of the LEDs included in the light sources 38 to 40 is driven by switching operations (ON/OFF) of transistors that are caused to operate when the CIS_LED_(R,G,B)_ON signals are supplied thereto. When the LEDs of the light sources 38 to 40 are driven at a maximum current, a CIS_RV signal as a reference voltage is kept constant and duration for supplying ON signals to the LEDs is adjusted, thereby adjusting light amounts of the light sources 38 to 40. When current values flowing in the LEDs are changed, the duration for supplying ON signals to the LEDs is kept constant, the CIS_RV signal as a reference voltage signal is driven according to pulse width modulation (PWM), and a driving duty of PMW is changed, thereby adjusting the light amounts of the light sources 38 to 40.

FIG. 8 is a block circuit diagram illustrating the control device 300 including an edge detecting circuit 42 used for detecting the edge of the recording medium S by the edge detecting device 29 according to the present embodiment. In the block circuit diagram of the control device 300 as illustrated in FIG. 8, the CIS 30 illustrated in FIG. 6 is used. In addition, the control device 300 includes a comparator 41, the edge detecting circuit 42, a CPU 44, a CIS control circuit 46, a threshold value setting circuit 43, and the LED current driving circuit 45 illustrated in FIG. 7.

A control signal is input from the CPU 44 to the CIS control circuit 46. Then, the CIS control circuit 46 supplies a readout clock (CIS_CLK) and a synchronizing signal (CIS_SI) to the CIS 30 and the edge detecting circuit 42. The CIS_SI is an output trigger of an analog signal (CIS_AN_OUT) for the CIS 30 and one period thereof corresponds to a charge accumulation time (readout time/sampling time) of one line. ON signals (CIS_LED_(G,R,B)_ON) and the reference voltage signal (CIS_RV) for determining current values of the LEDs are input to the LED current driving circuit 45 from the CIS control circuit 46 and the LED current driving circuit 45 supplies the driving currents for driving the LEDs to the CIS 30.

The threshold value setting circuit 43 receives a digital (High or Low) signal of one bit in accordance with presence or absence of the reflecting mirror 31 from the CIS control circuit 46 and supplies threshold value voltages X1 and X2 as threshold values in accordance with the presence or absence of the reflecting mirror 31 to the comparator 41.

The threshold value setting circuit 43 switches a signal input from the CIS control circuit 46, thereby enabling switching between the threshold value voltage X1 to be set when the reflecting mirror 31 is used and the threshold value voltage X2 to be set when the reflecting mirror 31 is not used. When the reflecting mirror 31 is used all the time in an attached state without being detached, the threshold value setting circuit 43 is not required and the threshold value voltage X1 is set.

The CIS 30 is supplied with the readout clock (CIS_CLK) and the synchronizing signal (CIS_SI) by the CIS control circuit 46 and driving currents of the light sources 38 to 40 by the LED current driving circuit 45, and outputs the analog signal (CIS_AN_OUT) to the comparator 41.

The analog signal (CIS_AN_OUT) from the CIS 30 and the threshold voltage from the threshold value setting circuit 43 are input to the comparator 41. Then, the comparator 41 converts the analog signal (CIS_AN_OUT) to a binary digital signal and outputs the binary digital signal to the edge detecting circuit 42 as a digital signal (CIS_DIN). In the conversion process, when the reflecting mirror 31 is used, the threshold value setting circuit 43 sets the threshold value voltage X1 to be set when the reflecting mirror 31 is used; and when the reflecting mirror 31 is not used, the threshold value setting circuit 43 sets the threshold value voltage X2 to be set when the reflecting mirror is not used. Furthermore, when the reflecting mirror 31 is used, the light amounts of the light sources 38 to 40 formed by the LEDs of three colors as illustrated in FIG. 6 are adjusted in accordance with the threshold value voltage X1 that has been set. On the other hand, when the reflecting mirror 31 is not used, the light sources 38 to 40 are driven with preset light amounts.

The edge detecting circuit 42 receives the digital signal (CIS_DIN) from the comparator 41 and the readout clock (CIS_CLK) and the synchronizing signal (CIS_SI) from the CIS driving circuit, and outputs a gate signal (P_EDGE) indicating the edge Sa of the recording medium S to the CPU 44.

The gate signal (P_EDGE) is input to the CPU 44 from the edge detecting circuit 42. The CPU 44 generates a count value from the gate signal via internal processing, calculates a difference value with respect to a reference pixel, and outputs the difference value to a system control circuit 47. The system control circuit 47 can correct registration in the main-scanning direction and calculate a skew amount based on the output difference value (that is, edge information). Furthermore, the CPU 44 switches light emitting duration of the light sources 38 to 40 in accordance with the presence or absence of the reflecting mirror 31 and adjusts the light amounts of the light sources 38 to 40 when the reflecting mirror 31 is used. Then, the CPU 44 outputs a control signal to the CIS control circuit 46.

Figure 9A:
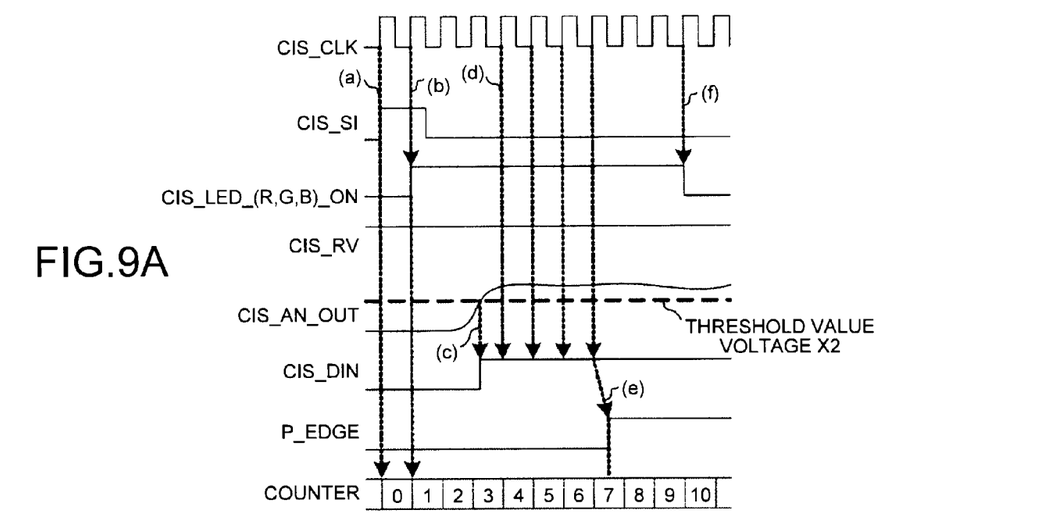
FIGS. 9A and 9B are timing charts illustrating operations of the edge detecting circuit.
Figure 9B:
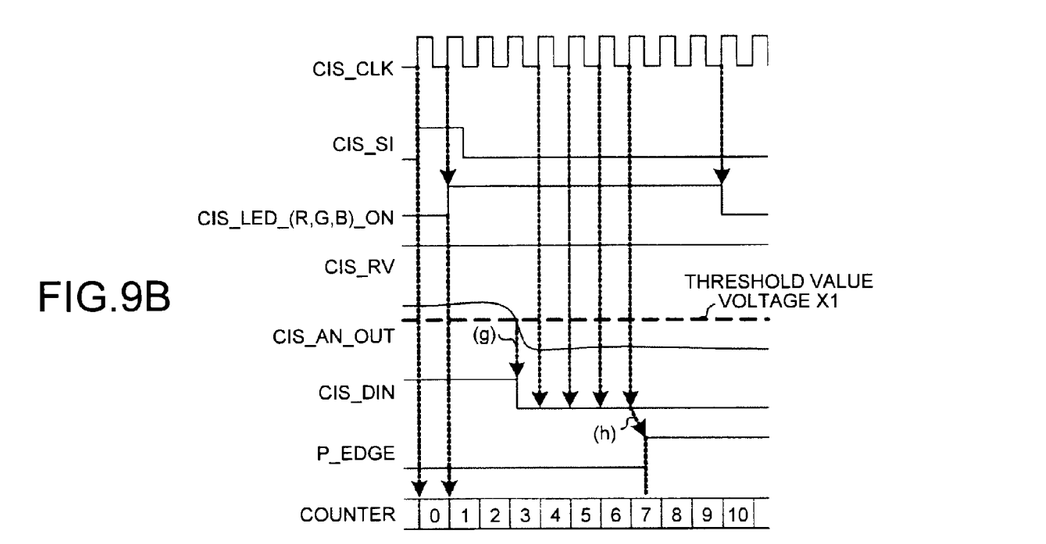

FIGS. 9A and 9B are timing charts illustrating an operation of the edge detecting circuit 42. FIG. 9A is a timing chart when the reflecting mirror 31 is not used and FIG. 9B is a timing chart when the reflecting mirror 31 is used. CIS_CLK denotes a readout clock, CIS_SI denotes a synchronizing signal and is a signal that is an output trigger of the analog signal (CIS_AN_OUT), CIS_LED_(R,G,B)_ON denote driving signals of the light sources 38 to 40, CIS_RV denotes a reference voltage signal, CIS_AN_OUT denotes an analog output from the CIS, CIS_DIN denotes a digital signal output from the comparator 41 as illustrated in FIG. 8, P_EDGE denotes a gate signal output from the edge detecting circuit 42 to the CPU 44 as illustrated in FIG. 8, and COUNTER denotes an internal counter of the CPU 44.

The COUNTER is reset to be "0" in synchronization with a rising of the CIS_CLK at timing at which the CIS_SI is High ((a) in FIG. 9A).

The CIS_LED_(R,G,B)_ON signals become High at a subsequent rising of the CIS_CLK and the light sources 38 to 40 are caused to emit light. Furthermore, the COUNTER starts to count at the same timing ((b) in FIG. 9A).

The CIS_DIN becomes High at timing at which the CIS_AN_OUT becomes higher than the threshold value voltage X2 ((c) in FIG. 9A).

A counter of a nozzle filter (not illustrated) starts counting in synchronization with a rising of the CIS_CLK at timing at which the CIS_DIN is High ("High" when the recording medium S is present) ((d) in FIG. 9A).

When the CIS_DIN is High for four contiguous pixels, the edge Sa of the recording medium S is determined to be present and the P_EDGE signal is set to High ((e) in FIG. 9A). With this operation, a value of the COUNTER is maintained. In FIG. 9A, the value of the COUNTER is maintained as "7".

Furthermore, the CIS_LED_(R,G,B)_ON become Low with an interval set by the CPU 44 and light emission from the light sources 38 to 40 is terminated ((f) in FIG. 9A).

Note that FIG. 9A illustrates a case where the reflecting mirror 31 is not used. In this case, when no recording medium S is present, the CIS_DIN is Low, and when the recording medium S is detected, the CIS_DIN becomes High. By contrast, FIG. 9B illustrates a case where the reflecting mirror 31 is used. In this case, contrary to the case where the reflecting mirror 31 is not used as illustrated in FIG. 9A, when no recording medium S is present, the CIS_DIN is High, and when the recording medium S is detected, the CIS_DIN becomes Low.

Therefore, the CIS_DIN becomes Low at a timing at which the CIS_AN_OUT becomes lower than the threshold value voltage X1 ((g) in FIG. 9B).

Furthermore, when the CIS_DIN is Low for four contiguous pixels, the edge Sa of the recording medium S is determined to be present and the P_EDGE signal is set to High ((h) in FIG. 9B).

As a reference pixel number from the timing when the CIS_SI becomes High until the P_EDGE becomes High, a value that is predetermined for each recording medium to be used by a system is stored in a memory (not illustrated). The CPU 44 detects the pixel number (COUNTER) on one recording medium basis from the timing when the CIS_SI becomes High until the P_EDGE becomes High and calculates a difference with respect to the reference pixel number.

Figure 10:
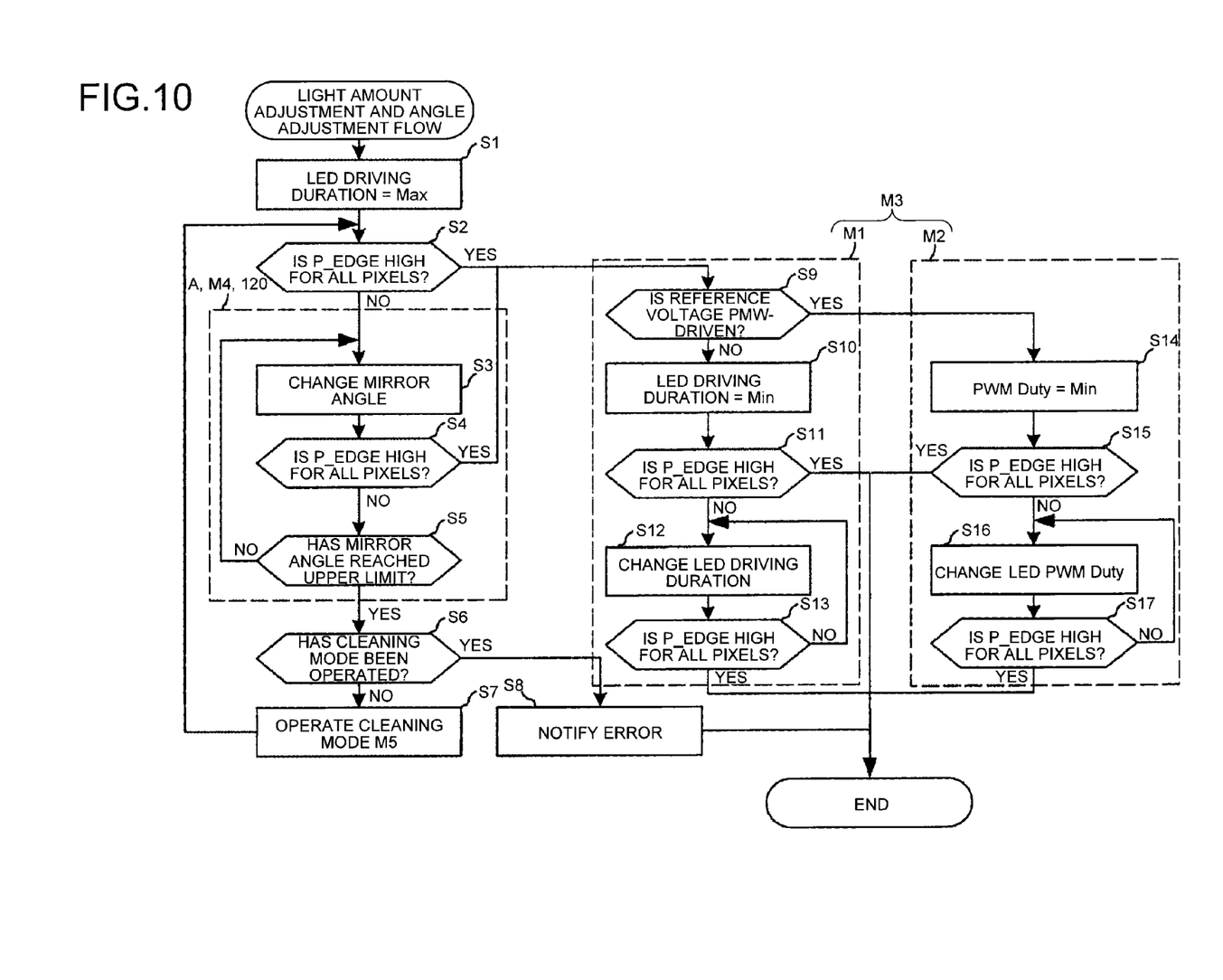
FIG. 10 is a flowchart illustrating a form of control contents of a light amount adjusting mode, an angle adjusting mode, and a cleaning mode.

FIG. 10 is a control flowchart illustrating contents of a light amount adjusting mode M3; and an angle adjusting mode M4 and a cleaning mode M5 of the reflecting mirror 31. It is to be noted that the flow is applied only when the reflecting mirror 31 is used. When the reflecting mirror 31 is not used, the light amounts are constant so that the flow is not applied thereto.

This control routine is performed on the CIS control circuit 46 as illustrated in FIG. 8. When the reflecting mirror 31 is attached to the edge detecting device 29, driving duration of the light sources 38 to 40 of the CIS 30 in FIG. 6 is set to MAX (a maximum value) (Step S1). As a signal for determining whether the reflecting mirror 31 is attached to the edge detecting device 29, an output from the light shielding sensor 34 is used. In this state, the light sources 38 to 40 are caused to emit light and it is determined whether the P_EDGE signal is High for all the pixels (Step S2). When the P_EDGE signal is High for all the pixels, angle adjustment is complete and a process proceeds to light source adjustment at Step S9.

When the P_EDGE signal is not High for all the pixels at Step S2, the stepping motor 33 as illustrated in FIG. 2 is driven to change the angle of the reflecting mirror 31 (Step S3). After the angle has been changed, the light sources 38 to 40 are caused to emit light and it is determined whether the P_EDGE signal is High for all the pixels (Step S4). Then, similarly to the case described above, when the P_EDGE signal is High for all the pixels, the angle adjustment is complete and the process proceeds to the light source adjustment at Step S9. These processes configure the angle adjusting mode M4.

When the P_EDGE signal is not High for all the pixels at Step S4, it is determined whether the angle of the reflecting mirror 31 has reached an upper limit of a changeable angle range (Step S5). When the angle of the reflecting mirror 31 does not reach the upper limit, the process returns to Step S3 and the processes similar to those above are performed. The processes at Step S3 to Step S5 as illustrated with a reference numeral A in the flow are initial setting operations of the reflecting mirror 31, correspond to the angle adjusting mode M4, and further serve as an operation of a contamination detecting unit 120. That is to say, it is determined that the recording medium is contaminated when the P_EDGE signal is not High for all the pixels.

At Step S5, when the reflecting mirror 31 has reached the upper limit of the angle range in which the reflecting mirror 31 can rotationally move, the reflecting surface 31a is determined to be contaminated and it is determined whether the cleaning mode M5 has been performed (Step S6). The determination on whether the cleaning mode M5 has been performed is made by referring to a value of the COUNTER that is stored when the cleaning mode M5 is performed, or by determining whether a flag having been set when the cleaning mode M5 is performed is present or not. When the cleaning mode M5 has not been performed, the cleaning mode M5 is performed (Step S7), and the process returns to Step S2 and the processes similar to those above are performed. The cleaning mode M5 is a mode in which the reflecting mirror 31 is rotated by the stepping motor 33 as illustrated in FIG. 2, the blower fan 350 is driven while the reflecting mirror 31 is rotated, thereby to remove dusts on the reflecting mirror 31 with the air blown from the blower fan 350. At Step S6, when the cleaning mode M5 has been already performed, an error message is displayed on the operator panel 27 illustrated in FIG. 1 (Step S8). Then, the light amount adjustment and the angle adjustment are completed.

After the adjustment of the angle of the reflecting mirror 31 has been normally ended, an LED light amount adjusting method is selected from among a plurality of methods that include a method for adjusting light emitting duration of the light sources 38 to 40; and a method for adjusting a Duty of PWM (changing a current value) by driving the reference voltage according to the PWM (Step S9). That is to say, either the first mode M1 or the second mode M2 can be selected. In the present embodiment, the PMV driving of the reference voltage is set as a default option. When the PMV driving of the reference voltage is not selected, it is determined that the adjustment of the light emitting duration of the light sources 38 to 40 is selected. In order for one of the first mode M1 and the second mode M2 is to be selected, a selecting switch or the like may be provided on the operator panel 27 as a selecting unit, and a selection may be determined by a designation signal that is input through the selecting switch.

When the light emitting duration of the light sources 38 to 40 are adjusted, driving duration of the light sources 38 to 40 are set to Min (a minimum value) (Step S10). In this state, the light sources 38 to 40 are caused to emit light and it is determined whether the P_EDGE signal is High for all the pixels (Step S11). When the P_EDGE signal is High for all the pixels, the light amount adjustment and the angle adjustment are completed. When the P_EDGE signal is not High for all the pixels, the driving duration of the light sources 38 to 40 are changed (driving duration is made longer) (Step S12). Thereafter, the light sources 38 to 40 are caused to emit light and it is determined whether the P_EDGE signal is High for all the pixels again (Step S13). Then, similarly to the processes as above, when the P_EDGE signal is High for all the pixels, the light amount adjustment and the angle adjustment are completed. When the P_EDGE signal is not High for all the pixels, the process returns to Step S11 and the flow similarly to the above is performed.

On the other hand, when the PWM driving is selected at Step S9, the PWM Duty of the reference voltage is set to Min (a minimum value) (Step S14). In this state, the light sources 38 to 40 are caused to emit light and it is determined whether the P_EDGE signal is High for all the pixels (Step S15). When the P_EDGE signal is High for all the pixels, the light amount adjustment and the angle adjustment are completed. When the P_EDGE signal is not High for all the pixels, the PWM Duties of the light sources 38 to 40 (LEDs) are changed (so as to be higher) (Step S16). Thereafter, the light sources 38 to 40 (LEDs) are caused to emit light again and it is determined whether the P_EDGE signal is High for all the pixels (Step S17). Then, in the same manner as the case described above, when the P_EDGE signal is High for all the pixels, the light amount adjustment and the angle adjustment are completed. When the P_EDGE signal is not High for all the pixels, the process returns to Step S16 and the processing that are the same as the above processing are performed until the P_EDGE signal becomes High for all the pixels. In the present embodiment, the light amount adjusting mode M3 is configured by the first mode M1 and the second mode M2.

Figure 11A:
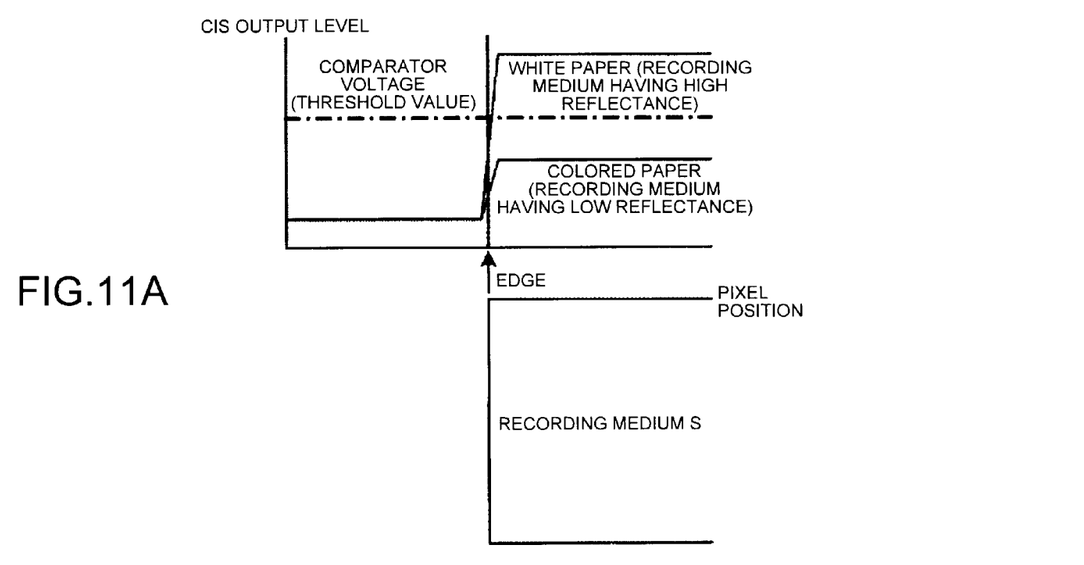
FIGS. 11A and 11B are graphs illustrating a relationship between an output level of the detecting unit and an arrangement of pixels of a photoelectric conversion element in the light receiving unit.
Figure 11B:
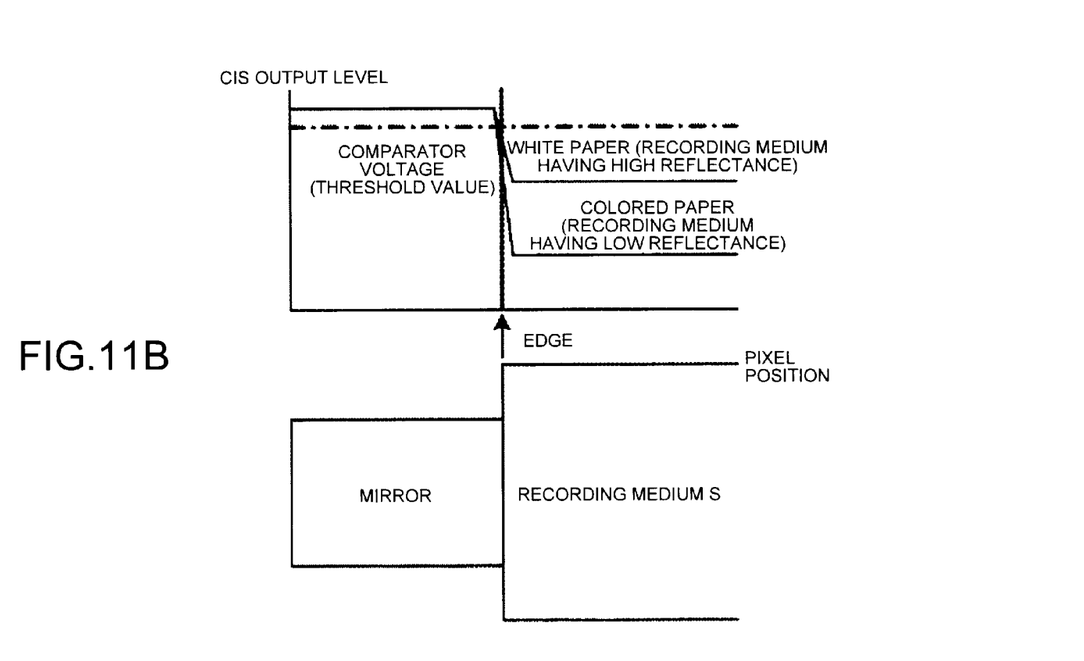

FIGS. 11A and 11B are graphs illustrating a relationship between an output level of the CIS 30 and a pixel position. FIG. 11A illustrates a case where the reflecting mirror 31 is not used. In FIG. 11A, a comparator voltage as the threshold value voltage X2 is set to a mean value between the maximum value and a minimum value of the CIS output level. Therefore, although a recording medium S having high reflectance such as a piece of white paper can be detected, a recording medium S having low reflectance such as a piece of colored paper cannot be detected. Furthermore, the CIS output level of a portion on which no recording medium S is present is at a Low level and the CIS output level of a portion on which the recording medium S is present is at a High level. A pixel of which output level becomes High from Low by exceeding the threshold voltage X2 is detected as an edge Sa of the recording medium S.

FIG. 11B illustrates a case where the reflecting mirror 31 is used. In FIG. 11A, a comparator voltage serving as the threshold value voltage X1 is set to a value lower than the maximum value of the CIS output level by about several hundreds mV. With this, the threshold value voltage X1 can be set to a value close to the maximum value of the CIS output level because a light emission amount is adjusted such that a light reception amount of the reflecting mirror 31 exceeds the threshold value voltage X1 for all the pixels at the time of the light amount adjustment. Furthermore, contrary to the case where the reflecting mirror 31 is not used, the CIS output level of a portion of the reflecting mirror 31 on which the recording medium S is not present is at a High level (upper limit value) and the CIS output level of a portion of the reflecting mirror 31 on which the recording medium S is present is at a Low level. Therefore, when the reflecting mirror 31 is used, a pixel of which output level changes from High to Low by falling below the threshold voltage X1 is detected as an edge Sa of the recording medium S.

When the reflecting mirror 31 is not used as illustrated in FIG. 11A, the light emitting duration of the light sources 38 to 40 are required to be longer so as to obtain more output from the CIS 30 in order to cope with the recording medium S having undesired reflectance property. On the other hand, when the reflecting mirror 31 is used, the reflecting mirror 31 has reflectance higher than that of the white paper and the light amounts of the light sources 38 to 40 can be adjusted in accordance with the output of the reflected light from the reflecting mirror 31. Therefore, in this case, the light emitting duration of the light sources 38 to 40 can be shortened in comparison with the case where the reflecting mirror 31 is not used. Therefore, load on the light sources 38 to 40 can be reduced to improve durability thereof, thereby making a usage period thereof longer. In addition, an edge of a recording medium S having different reflectance can be detected with high accuracy. Furthermore, the CIS_SI illustrated in FIG. 8 corresponding to a charge accumulation time (readout time/sampling time) of one line depends on the light emitting duration of the light sources 38 to 40. Therefore, if the light emitting duration of the light sources 38 to 40 is shortened, the charge accumulation time (readout time/sampling time) can also be shortened.

In the conventional method for detecting the edge of the recording medium S, light emitted from the light source (LED) of the CIS 30 is caused to be reflected by the recording medium S. Then, the reflected light is received by the CIS 30 and the recording medium S is determined to be present on a pixel that has received more light than a determination threshold value and the recording medium S is determined not to be present on a pixel that has received light equal to or less than the determination threshold value. Furthermore, a boundary between these pixels is detected to be the edge Sa of the recording medium S. Therefore, a light amount of reflected light reflected by the recording medium is insufficient depending on the light emission wavelength of the light source of the CIS 30 to be used or reflectance property of the recording medium S. In such a case, light with a light amount more than the threshold value cannot be received even on the portion on which the recording medium S is present and determination on whether or not the recording medium is present cannot be made. Therefore, it has been difficult to detect the edge Sa of the recording medium S.

However, as in the present embodiment, the reflecting mirror 31 as a form of a reflecting member having reflectance higher than that of the recording medium S to be used is mounted on a lower portion of the CIS 30 at an angle at which the reflecting mirror 31 can receive more reflected light. Furthermore, irradiation light emitted from the light sources 38 to 40 of the CIS 30 is reflected by the reflecting surface 31a having high reflectance and the recording medium S and the reflected light is received by the light receiving unit 36 of the CIS 30. With this, because the intensity of light reflected by the reflecting surface 31a having high reflectance is higher than that of light reflected by the recording medium S, no recording medium is determined to be present on a pixel that has received more reflected light than the threshold value X1 and the recording medium S is determined to be present on a pixel that has received less light. Therefore, a boundary between these pixels is detected to be the edge Sa of the recording medium S. Accordingly, even when a recording medium by which light is insufficiently reflected is used, the edge Sa of the recording medium S can be detected. Furthermore, the edge Sa of the recording medium S can be detected with high accuracy without depending on the light emission wavelength of the light sources 38 to 40 of the CIS 30 to be used or reflectance property of the recording medium S. Furthermore, light emission amounts required for detecting the edge can be reduced so as to shorten the light emitting duration of the light sources 38 to 40 formed by the LEDs. In addition, light emission intensities can be reduced so as to make the lifetime of the light sources 38 to 40 (LEDs) longer. Moreover, the light emitting duration of the light sources 38 to 40 is shortened so as to shorten the edge detection time.

In such a color printer that includes the edge detecting device 29, even when various recording media S having different reflectance values are used, edges thereof can be detected accurately in a short period of time. Therefore, the color printer has high paper handling capacity and can calculate a main-scanning registration correction amount on the various recording media S having different reflectance values and a skew amount accurately, thereby obtaining a preferable image.

In the present embodiment, the reflecting mirror 31 of the edge detecting device 29 is detachable from the sheet-metal frame 320. The control device 300 has threshold values X1 and X2 corresponding to cases where the reflecting mirror 31 is attached and not attached, respectively, and determines the edge Sa of the recording medium S using the threshold values X1 and X2. Therefore, the edge detecting device 29 can be attached to a color printer that does not include the edge detecting device 29 as an optional device, thereby enhancing versatility of the apparatus.

In the present embodiment, the contamination detecting unit 120 that detects contaminants on the reflecting surface 31a of the reflecting mirror 31 and the cleaning unit 100 are included. If the reflecting surface 31a is detected to be contaminated by the contamination detecting unit 120, the cleaning mode M5 is performed by using the cleaning unit 100. Accordingly, reflectance of the reflecting surface 31a can be stabilized and the edge Sa of the recording medium S can be detected more accurately. In addition, a main-scanning registration correction amount and a skew amount can be calculated more accurately, thereby obtaining a more preferable image.

In the present embodiment, the reflecting surface 31a of the reflecting mirror 31 is set at an angle at which the reflecting surface 31a reflects more reflected light emitted from the light sources 38 to 40 to pixels of the photoelectric conversion element in the light receiving unit 36. To be more specific, the light receiving unit 36 is formed such that the reflected light is concentrated on one point on the pixel of the photoelectric conversion element in the light receiving unit 36. Therefore, a light reception sensitivity of the light receiving unit 36 is enhanced so that the edge Sa of the recording medium S can be detected more accurately. In addition, a main-scanning registration correction amount and a skew amount can be calculated more accurately, thereby obtaining a more preferable image.

Furthermore, the angle adjusting mode M4 for controlling the reflecting surface 31a of the reflecting mirror 31 to be at an angle at which more light reflected by the reflecting surface 31a of the reflecting mirror 31 is reflected to the pixel of the photoelectric conversion element in the light receiving unit 36. Therefore, light reception sensitivity on the light receiving unit 36 is enhanced in combination with a shape of the reflecting surface 31a so that the edge Sa of the recording medium S can be detected more accurately. In addition, a main-scanning registration correction amount and a skew amount can be calculated more accurately, thereby obtaining a more preferable image.

According to the present embodiment, the intensity of reflected light reflected by the reflecting surface of the reflecting unit is higher than that of reflected light reflected by the recording medium. Therefore, it can be determined that a recording medium is not present on a pixel of a photoelectric conversion element when the pixel has received an amount of light that exceeds the threshold value and also that the recording medium is present on a pixel that has received light with an amount below the threshold value. Furthermore, by detecting a boundary between the pixels as an edge of the recording medium, an edge of a recording medium can be detected even if the recording medium that reflects insufficient light is used. Accordingly, edges of recording media of various types can be detected accurately in a short period of time without depending on the light emission wavelength of a light source or reflectance property of the recording media. Besides an edge of a recording medium can be detected accurately, a light emission amount required for detecting the edge is reduced, so that the light emission time of the light source can be shortened and the light emission intensity thereof can be reduced. This makes it possible to lengthen the lifetime of the light source.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An edge detecting device for detecting an edge of a moving recording medium, the edge detecting device comprising:
    a reflecting unit that includes a reflecting surface having reflectance higher than reflectance of the recording medium;
    a light source that irradiates the recording medium and the reflecting surface of the reflecting unit with light;
    a light receiving unit that includes a plurality of pixels of a photoelectric conversion element arranged in a width direction of the recording medium and receives reflected light that has been emitted from the light source and has been reflected by the recording medium and the reflecting surface of the reflecting unit on the pixels of the photoelectric conversion element;
    a control unit that determines a region of the pixels of the photoelectric conversion element that makes output higher than a preset determination threshold value in the light receiving unit as the edge of the recording medium;
    an angle adjusting unit that adjusts an angle of the reflecting surface of the reflecting unit; and
    a cleaning unit that cleans the reflecting surface of the reflecting unit,
    wherein the angle adjusting unit moves the reflecting surface to a position such that the cleaning unit can clean the reflecting surface.

2. The edge detecting device according to claim 1, wherein the reflecting unit is detachable from a detecting device main body, and
    the control unit has a determination threshold value corresponding to each of a case where the reflecting unit is attached to the detecting device main body and another case where the reflecting unit is not attached thereto and determines the edge of the recording medium by using the determination threshold value for each of the cases.

3. The edge detecting device according to claim 1, further comprising a light amount adjusting unit that adjusts a light amount of irradiation light emitted from the light source in accordance with output from the light receiving unit.

4. The edge detecting device according to claim 1, further comprising a contamination detecting unit that detects contaminant on the reflecting surface of the reflecting unit.

5. The edge detecting device according to claim 1, further comprising a first unit that detects one of presence and absence of the reflecting unit.

6. The edge detecting device according to claim 1, wherein the reflecting surface of the reflecting unit is set at an angle to reflect light emitted from the light source to the pixels of the photoelectric conversion element in the light receiving unit.

7. The edge detecting device according to claim 6, wherein the reflecting surface of the reflecting unit is formed such that reflected light reflected by the reflecting surface is concentrated linearly in a width direction of the pixels of the photoelectric conversion element in the light receiving unit.

8. The edge detecting device according to claim 3, wherein the light amount adjusting unit has a first mode in which the light source is controlled to be driven at a maximum electric current and a second mode in which an electric current to the light source is variably controlled.

9. The edge detecting device according to claim 3, wherein the edge detecting device has a light amount adjusting mode in which a light amount of light emitted from the light source is controlled in accordance with the output from the light receiving unit.

10. The edge detecting device according to claim 1, wherein the edge detecting device has an angle adjusting mode in which more reflected light reflected by the reflecting surface of the reflecting unit is controlled to be at an angle toward the pixels of the photoelectric conversion element of the light receiving unit.

11. The edge detecting device according to claim 5, wherein
the edge detecting device has a plurality of modes in which the edge of the recording medium is detected, and
the modes are selectively switched over based on a detection result from the first unit that detects one of presence and absence of the reflecting unit.

12. An image forming apparatus comprising:
a transfer unit that transfers a toner image formed on an image carrier;
a conveying path on which a recording medium housed in a paper feeding unit is conveyed toward the transfer unit, and
an edge detecting unit that is provided upstream of the transfer unit in a recording medium moving direction and detects an edge of a recording medium that is moving, wherein
the edge detecting unit is the edge detecting unit according to claim 1.

13. An edge detecting device according to claim 1, wherein the edge detecting device has a cleaning mode in which the reflecting surface of the reflecting unit is automatically cleaned.

14. The edge detecting device according to claim 1, wherein the cleaning unit includes a fan.

15. The edge detecting device according to claim 14, further comprising a blowing port which is disposed opposite the reflecting surface of the reflecting unit so that air sent from the fan blows the reflecting surface of the reflecting unit.

* * * * *